US008008083B2

(12) United States Patent
Hess et al.

(10) Patent No.: US 8,008,083 B2
(45) Date of Patent: Aug. 30, 2011

(54) NATRIURETIC PEPTIDES FOR DIAGNOSING CARDIAC COMPLICATIONS DUE TO CORONARY CATHETERIZATION

(75) Inventors: Georg Hess, Soergenloch (DE); Andrea Horsch, Mannheim (DE); Dietmar Zdunek, Tutzing (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 12/405,603

(22) Filed: Mar. 17, 2009

(65) Prior Publication Data

US 2010/0255590 A1  Oct. 7, 2010

Related U.S. Application Data

(63) Continuation of application No. PCT/EP2007/059597, filed on Sep. 12, 2007.

(30) Foreign Application Priority Data

Sep. 18, 2006  (EP) .................................... 06120814

(51) Int. Cl.
G01N 23/00  (2006.01)
(52) U.S. Cl. ............... 436/57; 436/536; 422/50; 435/4; 435/7.1; 435/7.8
(58) Field of Classification Search .................. None
See application file for complete search history.

(56) References Cited

U.S. PATENT DOCUMENTS 5,744,305 A  4/1998  Fodor et al.
7,358,055 B2*  4/2008  Valkirs et al. .................. 435/7.1

FOREIGN PATENT DOCUMENTS

WO  2002/089657 A3  11/2002
WO  2002/083913 A1  10/2004
WO  2006/087373 A1  8/2006

OTHER PUBLICATIONS

International Search Report issued Nov. 7, 2007 in PCT Application No. PCT/EP2007/059597.
International Preliminary Report on Patentability issued Nov. 7, 2008 in PCT Application No. PCT/EP2007/059597.
Abbas, Syed A. et al., Factors Associated with the Release of Cardiac Troponin T Following Percutaneous Transluminal Coronary Angioplasty, Clinical Cardiology, 1996, pp. 782-786, vol. 19.
Ala-Kopsala, Minna et al., Molecular Heterogeneity Has a Major Impact on the Measurement of Circulating N-Terminal Fragments of A- and B-Type Natriuretic Peptides, Clinical Chemistry, 2004, pp. 1576-1588, vol. 50, No. 9.
Bonow, Robert O., New Insights Into the Cardiac Natriuretic Peptides, Circulation, 1996, pp. 1946-1950, vol. 93.
Brueckmann, Martina et al., N-terminal pro-atrial natriuretic peptide as a biochemical marker of long-term interventional success after radiofrequency catheter ablation of paroxysmal supraventricular tachyarrhythmias, Clinical Chemistry and Laboratory Medicine, 2004, pp. 896-902, vol. 42, No. 8.
Costello, John M. et al., Effect of cardiopulmonary bypass and surgical intervention on the natriuretic hormone system in children, The Journal of Thoracic and Cardiovascular Surgery, Sep. 2005, pp. 822-829, vol. 130, No. 3.
Frigerio, Maria et al., Prevention and Management of Chronic Heart Failure in Management of Asymptomatic Patients, American Journal of Cardiology, May 8, 2003, pp. 4F-9F, vol. 91 (supplement), No. 9A.
Maisel, Alan S. et al., Cardiac biomarkers: a contemporary status report, Nature Clinical Practice, Jan. 2006, pp. 24-34, vol. 3, No. 1.
Mueller, Thomas et al., Long-term stability of endogenous B-type natriuretic peptide (BNP) and amino terminal proBNP (NT-proBNP) in frozen plasma samples, Clinical Chemistry Laboratory Medicine, 2004, pp. 942-944, vol. 42, No. 8.
Nolan, John P. and Skylar, Larry A., Suspension array technology: evolution of the flat-array paradigm, Trends in Biotechnology, Jan. 2002, pp. 9-12, vol. 20, No. 1.
Ricciardi, Mark J. et al., Visualization of Discrete Microinfarction After Percutaneous Coronary Intervention Associated With Mild Creatine Kinase-MB Elevation, Circulation, 2001, pp. 2780-2783, vol. 103.
Saadeddin, Salam M. et al, Detection of minor myocardial injury after successful percutaneous transluminal coronary angioplasty with or without stenting, Medical Science Monitor, 2000, pp. 708-712, vol. 6, No. 4.
Saleh, Nawsad et al., Usefulness of Preprocedural Serum N-Terminal Pro-Brain Natriuretic Peptide Levels to Predict Long-Term Outcome After Percutaneous Coronary Intervention in Patients With Normal Troponin T Levels, The American Journal of Cardiology, 2006, pp. 830-834, vol. 97.
Sundsfjord, J. A. et al., Identification and Plasma Concentrations of the N-Terminal Fragment of Proatrial Natriuretic Factor in Man, Journal of Clinical Endrocrinology and Metabolism, Mar. 1988, pp. 605-610, vol. 66, No. 3.
Tateishi, Jun et al., Transient Increase in Plasma Brain (B-Type) Natriuretic Peptide after Percutaneous Transluminal Coronary Angioplasty, Clinical Cardiology, 2000, pp. 776-780, vol. 23.
Wu, Alan H. B. et al., Analytical and Clinical Evaluation of the Bayer ADVIA Centaur Automated B-Type Natriuretic Peptide Assay in Patients with Heart Failure: A Multisite Study, Clinical Chemistry, 2004, pp. 867-873, vol. 50, No. 5.

* cited by examiner

*Primary Examiner* — Yelena Gakh
*Assistant Examiner* — Robert Xu

(57) ABSTRACT

The present invention discloses a method for diagnosing a cardiac complication in a patient due to coronary catheterization, comprising the steps of (a) obtaining at least one baseline sample from the patient during or after coronary catheterization, and then (b) obtaining at least one test sample from the patient after coronary catheterization, (c) determining a change of the level of an ANP-type peptide between the baseline sample and the test sample, wherein a significant decrease in the level of the ANP-type peptide according to step c) indicates a cardiac complication.

15 Claims, No Drawings

NATRIURETIC PEPTIDES FOR DIAGNOSING CARDIAC COMPLICATIONS DUE TO CORONARY CATHETERIZATION

RELATED APPLICATIONS

This application is a continuation of PCT/EP2007/059597 filed Sep. 12, 2007 and claims priority to EP 06120814.6 filed Sep. 18, 2006.

FIELD OF THE INVENTION

The present invention relates to diagnosing cardiac complications after any kind of coronary catheterization, e.g. angiography or, particularly, percutaneous coronary intervention (e.g. angioplasty or stent implantation). The present invention thus also provides risk stratification as to which patients may require closer monitoring and/or may benefit most from initiating early vigorous therapy after coronary catheterization.

BACKGROUND

An aim of modern medicine is to provide personalized or individualized treatment regimens. Those are treatment regimens which take into account a patient's individual needs or risks, e.g. by choosing a particular therapeutic or monitoring regimen.

Cardiovascular complications, particularly heart diseases, are the leading cause of morbidity and mortality in the Western hemisphere. In patients suffering or suspected of suffering from coronary heart disease are frequently a coronary catheterization is performed, e.g. for diagnostic or therapeutic purposes.

Coronary catheterization typically involves the introducing of a catheter into blood vessels belonging to the heart, particularly into the coronary arteries. The catheter is a long, thin, flexible tube. Examples for coronary catheterization include coronary angiography as well as percutaneous coronary intervention (PCI). In coronary angiography the catheter is typically used to introduce a contrast agent and then a picture (e.g. an X-ray picture or magnetic resonance picture) is taken to visualize the inner opening e.g. of the coronary arteries. In PCI, an angioplasty or stent implantation is performed by means of the catheter. A stent is typically a prosthesis which is capable of keeping a blood vessel open by mechanical strain against the wall of the vessel, particularly by expanding against the wall of the vessel. Thus, a stent can prevent a vessel from closing and thus prevent e.g. myocardial infarction. Prior to deployment, a stent is collapsed into a small diameter (e.g. as a folding grille) and is expanded at the position of interest.

Though coronary catheterization has become an important tool in diagnostics and therapy, it has been found that the procedure itself is associated with a relevant risk and may cause cardiac complications such as myocardial damage. This may be due e.g. to interruption of the normal blood flow during the procedure (e.g. side-branch occlusion) or due to damage to the wall of a blood vessel, e.g. by the catheter itself or by a stent which injures the wall of the vessel into which it is inserted. In fact, it has been described that more than 40 percent of patients undergoing coronary angioplasty have evidence of minor degrees of myocardial damage as evidenced by release of cardiac troponin T (cTnT), which is considered to be marker of myocardial necrosis (Abbas, S. A., Glazier, J. J., Wu, A. H., Dupont, C. et al. (1996). Factors associated with the release of cardiac troponin T following percutaneous transluminal coronary angioplasty. Clin. Cardiol., vol. 19, pp. 782-786). Slightly lower numbers, apparently based on clinical evidence of complications, are reported in the table 18-3, table 52-2, and table 52-3 of the textbook Braunwald's Heart Disease—A textbook of cardiovascular medicine (Braunwald (ed.) (2005)).

It seems that procedure-related myocardial injury does not always become clinically apparent. This is particularly troublesome as myocytes (the muscle cells which make up the heart muscle or myocard) are generally not capable of regenerating so that even minor myocardial injury should be avoided. Ricciardi et al. report that contrast-enhanced magnetic resonance imaging (MRI) provides an anatomical correlate to biochemical evidence of procedure-related myocardial injury, despite the lack of ECG changes or wall motion abnormalities (Ricciardi, M. J., Wu, E., Davidson, C. J., Choi, K. M. (2001). Visualization of discrete microinfarction after percutaneous coronary intervention associated with mild creatine kinase-MB elevation. Circulation, vol. 103, pp. 2780-2783). The same authors report that mild elevation of creatine kinase-MB (CK-MB) after PCI is the result of discrete microinfarction.

However, MRI is a costly technique requiring expensive equipment, which is not routinely available to monitor patients after coronary catheterization. Furthermore, creatine kinase-MB (CK-MB) is considered to be a marker indicating the presence of necrosis. Thus, CK-MB may indicate cardiac complications only after some possibly irreversible damage has already occurred.

Similarly, Saadeddin investigated cardiac troponin I (cTnI), cardiac troponin T (cTnT), and CK-MB after apparently successful percutaneous transluminal coronary angioplasty (PTCA) (Saadeddin, S. M., Habbab, M. A., Sobki, S. H., Ferns, G. A. (2000) Detection of minor myocardial injury after successful percutaneous transluminal coronary angioplasty with or without stenting. Med Sci Monit, vol. 6, pp. 708-712). They report that cTnI was a very sensitive marker in detecting myocardial injury after coronary angioplasty with or without stenting. However, also cTnI is considered to be a marker indicating the presence of necrosis. Thus, cTnI may indicate cardiac complications only after some possibly irreversible damage has already occurred.

In the already mentioned study, Abbas et al. have described that high-risk coronary lesions and both minor and major complications of angioplasty are associated with cTnT release (Abbas, S. A., Glazier, J. J., Wu, Dupont, C. et al. (1996). Factors associated with the release of cardiac troponin T following percutaneous transluminal coronary angioplasty. Clin. Cardiol., vol. 19, pp. 782-786). However, also cTnT is considered to be marker of myocardial necrosis and thus may indicates cardiac complications only after some possibly irreversible damage has already occurred.

BNP-type peptides (e.g. brain natriuretic peptide (BNP) and/or its N-terminal pro peptide fragment (NT-proBNP)) and their use as molecular or biochemical markers for diagnosis of certain disorders are known as such. In WO 02/089657, it has been suggested to measure brain natriuretic peptide (BNP) to diagnose myocardial infarction. In WO 02/083913 it has been suggested to use BNP to predict near-term morbidity or mortality in patients with congestive heart failure, myocardial infarction, ST-elevated myocardial infarction, or non-ST-elevated acute coronary syndromes.

An overview regarding biomarkers in cardiac disease has been given by Maisel et al. (Maisel, A. S., Bhalla, V., and Braunwald, E. (2006). Cardiac biomarkers: a contemporary status report, Nature Clinical Practice, vol. 3, pp. 24-34).

WO 2006/087373 describes a method for determining a cardiovascular complication in a patient diagnosing a cardiac disease in a patient presenting with symptoms of acute cardiac decompensation in which the information of the measured levels of NT-proANP and NT-proBNP is combined. In some patients in which the levels were measured subsequently an angiography was performed. After measurement, also a PCTA or a stent implantation was performed. However, the study did not address the problem of diagnosing a cardiac complication due to stent implantation.

Therefore, there is still a need to improve diagnosing cardiac complications due to coronary catheterization and to overcome the disadvantages of the state of the art. In particular, there is a need to provide further and improved diagnostic means and methods for diagnosing cardiac complications due to coronary catheterization. More particularly, there is a need to provide further means and methods which allow diagnosis of cardiac complications independent of myocardial necrosis or even before myocardial necrosis takes place.

SUMMARY OF THE INVENTION

The object of the invention is attained by a method for diagnosing a cardiac complication in a patient due to coronary catheterization, comprising the steps of
 (a) measuring the level of an ANP-Type peptide, or a variant thereof, in at least one baseline sample which has been obtained from the patient during or after coronary catheterization, and then
 (b) measuring the level of an ANP-Type peptide, or a variant thereof, in at least one test sample which has been obtained from the patient after coronary catheterization,
 (c) determining a change of the level of an ANP-Type peptide, or a variant thereof, between the baseline sample and the test sample, wherein a significant decrease in the level of the ANP-type peptide indicates a cardiac complication.

In a preferred embodiment, step c) is carried out as follows:
 c) determining a change of the level of an ANP-Type peptide, or a variant thereof, between the baseline sample and the test sample, and
 determining a change of the level of a BNP-Type peptide, or a variant thereof, between the baseline sample and the test sample, wherein a significant decrease in the level of the ANP-type peptide concomitant with a significant increase of a BNP-type peptide indicates a cardiac complication.

The method may also comprise the step of obtaining a body fluid or a tissue sample of the patient. Preferably, the level is determined in a body fluid or tissue sample of the patient. Preferably the level is determined in vitro.

If in the respective jurisdiction a method according to the invention is considered to relate also to embodiments which are exempt from patentability or industrial applicability due to relating to a diagnostic method practised on the human or animal body, then such included embodiment shall be exempt from the scope of protection.

The invention-provides methods and means, particularly markers, which allow to diagnose a cardiac complication due to coronary catheterization. Advantageously, the invention provides means and methods which allow diagnosis of cardiac complications independent of myocardial necrosis and/or even before myocardial necrosis takes place.

DETAILED DESCRIPTION OF THE INVENTION

In the context of the invention it has been observed that a decrease in the level of the ANP-type peptide after coronary catheterization indicates a cardiac complication. This finding has been quite unexpected as in other cardiovascular complications it is actually an increase but not a decrease of ANP-type peptides which indicates the presence of a complication. Furthermore, it has been realized that ANP-type peptides provide reasonable diagnostic information even though one may expect that the procedure itself would lead to considerable disturbance of the levels of ANP-type peptides. Advantageously, it has been observed that a decrease of the ANP-type peptide can be observed already early after a cardiac complication following coronary catheterization. Thus, the level of the ANP-type peptide provides earlier diagnostic information than markers of necrosis. Such early diagnostic information may allow early therapeutic intervention in order to minimize possible necrosis. Thus, the invention allows to start therapy earlier and/or in a more vigorous manner. It should be noted that according to the findings made in the course of the invention it is possible to diagnose an additional cardiac complication even in patients who are already suffering from cardiovascular complications which necessitated the coronary catheterization. Such additional cardiac complication is particularly a cardiac complication caused, directly or indirectly, by the coronary catheterization.

In the context of the invention it has also been observed that diagnosis can be further improved and/or confirmed by measuring the level of a BNP-type peptide. Interestingly, in the case of BNP-type peptides, an increase is indicative of a cardiac complication instead of a decrease (as in the case of an ANP-type peptide). Therefore, in a preferred embodiment of the invention, the diagnostic information of the levels of ANP-type and BNP-type peptides is combined (see further below for details).

Advantageously, the diagnostic information provided by the invention also allows to diagnose a cardiac complication which is asymptomatic or clinically not apparent. E.g. the invention also allows to diagnose a cardiac complication already before it becomes symptomatic or clinically apparent. The invention also allows to diagnose a myocardial ischemia before necrosis occurs. Consequently, the present invention also relates to determining a risk of suffering from a cardiac complication, particularly necrosis, due to coronary catheterization. In patients with diagnosis of myocardial ischemia and/or high risk of necrosis, early vigorous therapy or further diagnosis or monitoring can be initiated in order to avoid such necrosis.

The invention provides very sensitive diagnostic information and the information can also be easily quantified. Therefore, the invention may also be used for quality assessment or quality monitoring of coronary catheterization, e.g. to compare different methods of catheterization, to compare the performance of different clinics or departments, or in studies to develop new or improved methods of catheterization or subsequent treatment. Advantageously, the invention provides such information at a level of complications which are clinically not apparent or asymptomatic. Therefore, statistically significant information about increasing or reducing the number of cardiac complications can be obtained at lower patient numbers and lower numbers of clinically apparent or symptomatic events. Thus, such studies can be performed with less risk and/or fewer patients. The information is easily standardizable and can be easily or automatically analyzed by automated means, so that a routine quality assessment and/or alert system can be easily established.

The methods and means provided herein are simple, fast, and relatively inexpensive. Advantageously, tools for measuring the levels of ANP-type and BNP-type peptides are already commercially available so that in many cases no additional laboratory equipment will be needed for measurement.

The term "coronary catheterization" is known to the person skilled in the art. In the context of the invention, the term particularly relates to any kind of diagnostic or therapeutic intervention involving the introducing of a catheter into blood vessels belonging to the heart, particularly into the coronary arteries.

According to the invention, the term "coronary catheterization" is considered to include diagnostic (e.g. coronary angiography) as well as therapeutic catheterization (e.g. percutaneous coronary intervention (PCI)).

Particularly, diagnostic coronary catheterization as defined according to the invention allows to recognize e.g. occlusion, stenosis, restenosis, thrombosis or aneurysmal enlargement the coronary artery lumens, heart chamber size, heart muscle contraction performance and some aspects of heart valve function. Important internal heart and lung blood pressures, not measurable from outside the body, can be accurately measured during the test. The relevant problems that the test deals with most commonly occur as a result of advanced atherosclerosis, atheroma activity within the wall of the coronary arteries. Less frequently, other issues, valvular, heart muscle or arrhythmia issues are the primary focus of the test. Coronary artery luminal narrowing reduces the flow reserve for oxygenated blood to the heart, typically producing intermittent angina if very advanced; luminal occlusion usually produces a heart attack.

The term "coronary angiography" is known to the person skilled in the art. More particularly, it is a medical imaging technique in which a picture (e.g. an X-ray picture or magnetic resonance picture) is taken to visualize the inner opening of blood filled structures, e.g. arteries, veins and the heart chambers, particularly coronary arteries. The image of the blood vessels is called an angiograph, or more commonly, an angiogram. As blood has the same radiodensity as the surrounding tissues, a radiocontrast agent (which absorbs X-rays) may added to the blood to make angiography visualization by X-ray possible. A long, thin, flexible tube called a catheter is used to administer a contrast agent at the desired area to be visualized. The catheter is threaded into an artery e.g. in the groin or forearm, and the tip is advanced through the arterial system into one of the two major coronary arteries. The angiographic image is typically a shadow picture of the openings within the cardiovascular structures carrying blood (e.g. by means of the contrast agent within the blood). The images may be taken as still images or motion images. Motion images may also show the speed of blood (actually the speed of radiocontrast within the blood) traveling within the blood vessel.

Therapeutic coronary catheterization according to the invention relates to any kind of coronary catheterization for the purpose of treating a disorder or disease, including e.g. coronary angioplasty (particularly balloon dilatation) and stent implantation.

Therapeutic catheterization may be performed during an conventional surgery or microinvasively as PCI (percutaneous coronary intervention), which relates to any kind of angioplasty or stent implantation performed under microinvasive conditions. Microinvasive coronary angioplasty is also known as "transluminal coronary angioplasty". The invention is particularly useful in the context of PCI.

The terms "stent" and "stent implantation" are known to the person skilled in the art. Particularly, stent implantation relates to introducing any kind of stent into a coronary artery. A stent is particularly understood as any kind of prosthesis which is capable of keeping a blood vessel open by mechanical strain against the wall of the vessel, particularly by expanding against the wall of the vessel. Prior to deployment, a stent is collapsed into a small diameter (e.g. as a folding grille). A stent can be self-expanding (e.g. a wall stent) or it can be expanded by additional means, e.g. a an inflatable balloon (e.g. Palmaz-stent). The stent can be made from any kind of material. Currently, most stents in clinical practice are made from metal. Typically, after expansion, the stent is affixed to the vessel wall by its own radial tension. Stents are most commonly inserted under fluoroscopic guidance or endoscopy, which are microinvasive procedures that are generally less invasive than conventional surgery. This makes stents suitable for patients with advanced disease or those for whom otherwise the risk of major surgery is high. In addition, general anesthesia is usually not required for stent insertion.

Particularly, the invention relates to diagnosing a therapeutic coronary catheterization, as the such catheterization is associated with a higher risk of cardiac complication than diagnostic catheterization. More particularly, the invention relates to coronary angioplasty (particularly balloon dilatation) and/or stent implantation.

The person skilled in the art understands what is meant if a cardiac complication is considered to occur "due to" coronary catheterization. Particularly, a cardiac complication will generally considered to have occurred "due to" coronary catheterization if it occurs within 12 hours, 1 day, 2 days, 4 days, or one week after coronary intervention. Alternatively or additionally, cardiac complication will generally be considered to have occurred due to coronary catheterization if the complication is causally related to coronary intervention, whether directly or indirectly. Indications for such causal connection may include e.g. (i) a close time-relationship between catheterization and complication (see immediately above), and/or (ii) a connection of the kind of complication and catheterization (e.g. any additional myocardial ischemic or myocardial necrosis will generally be considered due to coronary catheterization as they are typical or frequent complications of catheterization), and/or (iii) a connection between the region of the cardiac tissue affected and the region in which catheterization was performed (e.g. myocardial ischemia or necrosis is found downstream of the blood flow of the investigated vessel or of a collateral which has become temporarily occluded during catheterization).

The invention takes advantage of certain biochemical or molecular markers. The terms "biochemical marker" and "molecular marker" are known to the person skilled in the art. In particular, biochemical or molecular markers are gene expression products which are differentially expressed (i.e. upregulated or downregulated) in presence or absence of a certain condition, disease, risk, or complication. Usually, a molecular marker is defined as a nucleic acid (such as an mRNA), whereas a biochemical marker is a protein, polypeptide or peptide. The level of a suitable biochemical or molecular marker can indicate the presence or absence of the condition, disease, or complication, and thus allow diagnosis.

The present invention particularly takes advantage of ANP-type and BNP-type peptides as biochemical or molecular markers. Also the use of any combinations of ANP-type and BNP-type peptides as biochemical markers is considered in the context of the present invention.

ANP-type and BNP-type peptides belong to the group of natriuretic peptides (see e.g. Bonow, R. O. (1996). New insights into the cardiac natriuretic peptides. Circulation 93: 1946-1950).

ANP-type peptides comprise pre-proANP, proANP, NT-proANP, and ANP.

BNP-type peptides comprise pre-proBNP, proBNP, NT-proBNP, and BNP.

Preferred ANP-type peptides according to the present invention are NT-proANP, proANP, ANP, or variants thereof. The most preferred ANP-type peptides according to the present invention are NT-proANP or variants thereof. Preferred BNP-type peptides according to the present invention are NT-proBNP, proBNP, BNP, or variants thereof. The most preferred BNP-type peptides according to the present invention are NT-proBNP or variants thereof.

ANP and BNP are the active hormones and have a shorter half-life than their respective inactive counterparts, NT-proANP and NT-proBNP. The pre-pro peptide (134 amino acids in the case of pre-proBNP) comprises a short signal peptide, which is enzymatically cleaved off to release the pro peptide (108 amino acids in the case of proBNP). The pro peptide is further cleaved into an N-terminal pro peptide (NT-pro peptide, 76 amino acids in case of NT-proBNP) and the active hormone (32 amino acids in the case of BNP).

Preanalytics are more robust with NT-proBNP than with BNP, allowing easy transportation of the sample to a central laboratory (Mueller T, Gegenhuber A, Dieplinger B, Poelz W, Haltmayer M. Long-term stability of endogenous B-type natriuretic peptide (BNP) and amino terminal proBNP (NT-proBNP) in frozen plasma samples. Clin Chem Lab Med 2004; 42: 942-4.). Blood samples can be stored at room temperature for several days or may be mailed or shipped without recovery loss. In contrast, storage of BNP for 48 hours at room temperature or at 4° Celsius leads to a concentration loss of at least 20% (Mueller T, Gegenhuber A, et al., Clin Chem Lab Med 2004; 42: 942-4, supra; Wu A H, Packer M, Smith A, Bijou R, Fink U, Mair J, Wallentin L, Johnston N, Feldcamp C S, Haverstick D M, Ahnadi C E, Grant A, Despres N, Bluestein B, Ghani F. Analytical and clinical evaluation of the Bayer ADVIA Centaur automated B-type natriuretic peptide assay in patients with heart failure: a multisite study. Clin Chem 2004; 50: 867-73.).

Either measurement of the active or the inactive form can be advantageous, depending on the time-course of interest and the analytical equipment or storage conditions available.

The term "variants" in this context relates to peptides substantially similar to said peptides. The term "substantially similar" is well understood by the person skilled in the art. In particular, a variant may be an isoform or allele which shows amino acid exchanges compared to the amino acid sequence of the most prevalent peptide isoform in the human population. Preferably, such a substantially similar peptide has a sequence similarity to the most prevalent isoform of the peptide of at least 80%, preferably at least 85%, more preferably at least 90%, most preferably at least 95%. Substantially similar are also degradation products, e.g. proteolytic degradation products, which are still recognized by the diagnostic means or by ligands directed against the respective full-length peptide. The term "variants" is also meant to relate to splice variants.

The term "variant" also relates to a post-translationally modified peptide such as glycosylated peptide. A. "variant" is also a peptide which has been modified after collection of the sample, for example by covalent or non-covalent attachment of a label, particularly a radioactive or fluorescent label, to the peptide.

Examples of particular variants and methods for their measurement are known (see e.g. Ala-Kopsala, M., Magga, J., Peuhkurinen, K. et al. (2004): Molecular heterogeneity has a major impact on the measurement of circulating N-terminal fragments of A-type and B-type natriuretic peptides. Clinical Chemistry, vol. 50(9), 1576-1588).

Other embodiments of the invention include the measuring of different markers in combination, simultaneously or non-simultaneously, e.g NT-proANP in combination with NT-proBNP, proANP in combination with proBNP, ANP in combination with NT-proBNP, or BNP in combination with NT-proANP.

Additionally, the level of at least one marker chosen from the group consisting of (a) markers of inflammation or variants thereof, and (b) markers of ischemia and variants thereof may be measured.

Measuring such additional marker may increase the selectivity and specificity of diagnosis. It may also serve to confirm a diagnosis established by measuring the level of an ANP-typ peptide and/or a BNP-type peptide. Such additional markers may also help to stratify a diagnosis further according the primary cause of the cardiac complication (e.g. primarily inflammation or ischemia/necrosis). Further treatment can then be adapted more specifically to the needs of the individual patient.

Markers of inflammation according to the invention include any markers indicative of an inflammatory process, particularly a vascular or arterial inflammatory process. Particularly, markers of inflammation according to the present invention comprise inflammatory active cytokines. Examples for markers of inflammation include interferons (e.g. interferon gamma), interleukins (e.g. IL-1, IL-6, IL-8), Tumor necrosis factor alpha (TNF-alpha)), CRP (C-reactive protein), myeloperoxidase (MPO), monocyte chemoattractant protein-1 (MCP-1), matrix metalloproteinases (MMPs). CRP may also be measured as "hsCRP" (high-sensitivity C-reactive protein), which means that it is measured by a highly sensitive test, e.g. available for Roche Elecsys or Cobas Analyzers (Roche Diagnostics), e.g. cat. no. 11972855 (Roche Diagnostics). Cut-off values and/or reference levels regarding said markers are well-known in the art.

Markers of necrosis according to the invention comprise any markers indicative of cell death, particularly myocardial cell death. Such necrosis may be caused ischemia, e.g. due to temporary or permanent occlusion of a blood vessel. Examples for markers of necrosis include cardiac troponins (e.g. cTnI and cTnT), creatine kinase MB (CK-MB), and ischemic modified albumin (IMA). Preferably, the marker of necrosis is chosen from the group consisting of cTnI, cTnT, and CK-MB. If coronary catheterization is performed during conventional surgery, CK-MB may be a slightly less preferred marker, as it may also indicate injury to skeletal muscle. cTnT may also be measured as "hsTnT" (high-sensitivity troponin T), which means that it is measured by a highly sensitive test, e.g. available for Roche Elecsys or Cobas Analyzers (Roche Diagnostics). Cut-off values and/or reference levels regarding said markers are well-known in the art, e.g. a typical reference level for cTnT is 10 pg/ml in blood plasma). Suitable levels may also be derived from the levels mentioned in the publications referenced in this specification (e.g. Abbas et al., Ricciardi et al., Saadeddin et al.) whose content in this respect is expressly incorporated into this specification by reference.

With respect to the term "variants" in the context of such additional markers the explanations given in the context of ANP-type and/or BNP-type peptides apply analogously.

The terms "baseline sample" and "test sample" are known to the person skilled in the art. The "baseline sample" is particularly understood as a sample which is obtained in order to reflect the level of the respective marker during coronary catheterization or at the end of coronary catheterization. Therefore, it is clear to the person skilled in the art that the baseline sample is preferably obtained during coronary catheterization or without undue delay after coronary catheterization. Preferably, the "baseline sample" is taken shortly or immediately after coronary catheterization. Preferably, the "baseline sample" is taken not later than 2 hours, more preferably not later than 1.5 hours, more preferably not later than 1 hour, more preferably not later than 0.5 hours after coronary catheterization, these time-periods being computed from the end of the catheterization procedure, preferably from the end of removing the catheter from the coronary vessel. In the case of stent implantation a suitable time may be e.g. immediately before or at the time of administering clopidogrel, ticlopidin, or another thrombocyte aggregation inhibitor after stent implantation (such thrombocyte aggregation inhibitors are currently routinely administered shortly after stent implantation in order to prevent occlusion of the stent).

The "test sample" is particularly understood as a sample which is obtained in order to reflect a change of the level of the respective marker as compared to the baseline sample. Preferably, the test sample is taken not too late after coronary catheterization (in order to allow timely diagnosis) but also not too early after the baseline sample (in order to observe a sufficiently significant change to allow for diagnosis). E.g. the "test sample" may be obtained within 4 to 48 hours, more preferably within 4 to 36 hours, 4 to 30 hours, 4 to 24 hours, 5 to 24 hours, 5 to 12 hours, or most preferably at approximately 6 hours after coronary catheterization. Preferably, at least one further test sample is obtained in order to confirm the change of the level and/or diagnosis. Such further test sample may be obtained e.g. within 6 to 72 hours, more preferably 8 to 48 hours, 12 to 36 hours, 20 to 30 hours, or most preferably at approximately 1 day or 24 hours after coronary catheterization.

The samples are preferably suitable body fluid samples as known to the person skilled, in the art and laid out elsewhere in the specification.

The above-mentioned additional markers (markers for inflammation or markers for necrosis) may be measured in the same samples as the ANP-type peptide or BNP-type peptide. However, the levels of some additional markers may change more slowly than the level of the ANP-type or BNP-type peptide, particularly more slowly than the ANP-type peptide. Therefore, it may be advantageous to measure the level of such additional markers additionally in a further test sample after a first test sample has been taken, e.g. within 6 to 72 hours, preferably within 8 to 72 hours, more preferably within 12 to 48 hours after coronary catheterization. The level of such additional markers may be interpreted according to a change in relation to a level measured in a baseline sample (a significant increase indicating the presence of inflammation or necrosis, respectively) or as an absolute level. In the latter case it may be unnecessary to measure the level in the baseline sample. However, additional measurement in a baseline sample is preferred. Absolute levels indicating the presence of inflammation or necrosis are known for the respective additional markers, see e.g. Abbas et al. (1996), Clin. Cardiol., vol. 19, pp. 782-786; Ricciardi et al. (2001), Circulation, vol. 103, pp. 2780-2783; and Saadeddin et al. (2000), Med Sci Monit, vol. 6, pp. 708-712; all cited above. For further guidance see also Maisel, A. S. et al. (2006), Nature Clinical Practice, vol. 3, pp. 24-34; also cited above.

The term "cardiac complication" is known to the person skilled in the art.

Patients suffering from a cardiac complication may be individuals suffering from stable angina pectoris (SAP) and individuals with acute coronary syndromes (ACS). ACS patients can show unstable angina pectoris (UAP) or these individuals have already suffered from a myocardial infarction (MI). MI can be an ST-elevated MI or a non-ST-elevated MI. The occurring of an MI can be followed by a left ventricular dysfunction (LVD). Finally, LVD patients undergo congestive heart failure (CHF) with a mortality rate of roughly 15%.

Cardiac cardiac complications according to the present invention also include coronary heart disease, heart valves defects (e.g. mitral valve defects), dilatative cardiomyopathy, hypertroph cardiomyopathy, and heart rhythm defects (arrythmias).

The term "coronary heart disease", abbreviated CHD, also called coronary artery disease (CAD) or atherosclerotic heart disease, is known to the person skilled in the art. Particularly, CHD is the result of the accumulation of atheromatous plaques within the walls of the arteries that supply the myocardium (the muscle of the heart). While the symptoms and signs of coronary heart disease are noted in the advanced state of disease, most individuals with coronary heart disease show no evidence of disease for decades as the disease progresses before the first onset of symptoms, often a "sudden" heart attack, finally arise. After decades of progression, some of these atheromatous plaques may rupture and (along with the activation of the blood clotting system) start limiting blood flow to the heart muscle.

The cardiac complication according to the present invention may be "symptomatic" or "asymptomatic". Cardiac complications can cause symptoms, which have been classified into a functional classification system according to the New York Heart Association (NYHA). Patients of Class I have no obvious symptoms of cardiovascular disorder. Physical activity is not limited, and ordinary physical activity does not cause undue fatigue, palpitation, or dyspnea (shortness of breath). Patients of class II have slight limitation of physical activity. They are comfortable at rest, but ordinary physical activity results in fatigue, palpitation, or dyspnea. Patients of class III show a marked limitation of physical activity. They are comfortable at rest, but less than ordinary activity causes fatigue, palpitation, or dyspnea. Patients of class IV are unable to carry out any physical activity without discomfort. They show symptoms of cardiac insufficiency at rest. If any physical activity is undertaken, discomfort is increased.

Another functional classification is the grading of angina pectoris by the Canadian Cardiovascular Society (CCS) classification system:

Class I: Ordinary physical activity does not cause angina, such as walking, climbing stairs. Angina [occurs] with strenuous, rapid, or prolonged exertion at work or recreation.

Class II: Slight limitation of ordinary activity. Angina occurs on walking or climbing stairs rapidly, walking uphill, walking or stair climbing after meals, or in cold, or in wind, or under emotional stress, or only during the few hours after awakening. Walking more than two blocks on the level and climbing more than one flight of ordinary stairs at a normal pace and in normal condition.

Class III: Marked limitations of ordinary physical activity. Angina occurs on walking one to two blocks on the level and climbing one flight of stairs in normal conditions and at a normal pace.

Class IV: Inability to carry on any physical activity without discomfort—angina symptoms may be present at rest.

Accordingly, patients suffering from cardiovascular disorders can be divided into individuals showing no clinical symptoms and those with symptoms (e.g. dyspnea).

Another characteristic of cardiovascular disorders can be the "left ventricular ejection fraction" (LVEF) which is also known as "ejection fraction". People with a healthy heart usually have an unimpaired LVEF, which is generally described as above 50%. Most people with a systolic heart disease which is symptomatic generally have an LVEF of 40% or less.

In the context of the present invention "cardiac complication" particularly relates to any kind of disorder or dysfunction of the heart or the coronary heart vessels. More particularly, "cardiac complication" relates to any kind of coronary heart disease, more particularly to a coronary heart disease which is not clinically apparent and/or asymptomatic. More particularly, "cardiac complication" relates to a coronary heart disease which is not clinically apparent and/or which is asymptomatic as compared to any kind of coronary heart disease present in the patient before coronary catheterization. Thus, the term "cardiac complication" particularly relates to an additional coronary heart disease which does not cause an increase in the level of the NYHA and/or CCS class as compared to the NYHA and/or CCS class of the patient before coronary catheterization. The term "clinically apparent" in this context particularly means that the coronary heart disease does not cause a change in the shape of the electrocardiogram.

Examples for cardiac complications which are typically not clinically apparent or asymptomatic include minor ischemia, minor necrosis, and/or microinfarction. Thus, present invention is particularly useful in the diagnosis of minor ischemia, minor necrosis, and/or microinfarction.

The invention also allows to diagnose a myocardial ischemia before necrosis occurs. Consequently, the present invention also relates to determining a risk of suffering from a cardiac complication, particularly necrosis, due to coronary catheterisation. In patients with diagnosis of myocardial ischemia and/or high risk of necrosis, early vigorous therapy or further diagnosis or monitoring can be initiated in order to avoid such necrosis. More particularly the term "before necrosis occurs" is understood as relating to a time before the level of a marker of necrosis, more particularly troponin T, has become significantly increased.

Diagnosing according to the present invention includes determining, monitoring, confirmation, subclassification and prediction of the relevant disorder or risk. Determining relates to becoming aware of a disorder or risk. Monitoring relates to keeping track of an already diagnosed disorder or risk, e.g. to analyze the progression of a disorder or risk or the influence of a particular treatment on the progression of a disorder or risk. Confirmation relates to the strengthening or substantiating a diagnosis already performed using other indicators or markers. Subclassification relates to further defining a diagnosis according to different subclasses of the diagnosed disorder or risk, e.g. defining according to mild and severe forms of the disorder. Prediction relates to prognosing a disorder or risk before other symptoms or markers have become evident or have become significantly altered. Prediction may also be understood as specifying a risk or likelihood that a particular disorder or risk will take place within a given time-span.

As will be understood by those skilled in the art, such diagnosis is usually not intended to be correct for 100% of the subjects to be diagnosed. The term, however, requires that a statistically significant portion of subjects can be diagnosed with respect to relevant disorder, risk or need. Whether a portion is statistically significant can be determined without further ado by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001.

The term "patient" according to the present invention relates to a healthy individual, an apparently healthy individual, or, particularly, an individual having a disease or suspected of having a disease, particularly coronary heart disease. The individual as meant herein, preferably, has an anatomically normal heart, i.e. a heart without congenital abnormalities. Preferably, the term relates to an individual without a congenital anatomic heart defect. Congenital anatomic heart defects in this context are, preferably, Aortic Stenosis, Atrial Septal Defect (ASD), Atrioventricular Canal Defect, Coarctation of the Aorta, Hypoplastic Left Heart Syndrome, Pulmonary Atresia, Pulmonary Stenosis, Tetralogy of Fallot (TOF), Total Anomalous Pulmonary Venous Connection, Tricuspid Atresia, Truncus Arteriosus, Ventricular Septal Defect (VSD).

Diagnosis according to the present invention is preferably done by use of a diagnostic means. A diagnostic means is any means that allows to measure the level, amount, or concentration of a substance of interest, particularly a peptide or polypeptide of interest, more particularly an ANP-type and/or a BNP-type peptide.

Methods and diagnostic means which can be used to measure the levels of the respective peptides are known to the person skilled in the art. These methods include microplate ELISA-based methods, fully-automated or robotic immunoassays (available for example on Elecsys™ or Cobas™ analyzers), CBA (an enzymatic Cobalt Binding Assay, available for example on Roche-Hitachi™ analyzers), and latex agglutination assays (available for example on Roche-Hitachi™ analyzers). The methods and means for measurement also include Point-of-care devices, such as the Cardiac Reader™ (available from Roche Diagnostics).

Point-of-care devices are generally understood as devices which enable measuring at the patient bedside. Preferably, point-of-care devices are understood as miniaturized or portable devices. An example is the Cardiac Reader™ (available from Roche Diagnostics), in combination e.g. with test strips for NT-proBNP (available as "Cardiac proBNP" from Roche Diagnostics). Such test may employ two (preferably monoclonal) antibodies directed against the peptide of interest (e.g. an ANP-type and/or a BNP-type peptide). The antibodies can be identical to the antibodies used e.g. in the Elecsys™ or Cobas™ assays. E.g. the first antibody is labeled with biotin while the second antibody is labeled with gold particles. The test can be started by adding a small amount (e.g. 150 µl) of blood sample onto the test strip (e.g. into a sample well of the test strip). The erythrocytes in the sample may be separated from the remaining plasma before or after addition to the test strip, e.g. if the sample flows through a suitable fleece (e.g. a glass fiber fleece). Said separating means (e.g. fleece) is preferably part of the test strip. The antibodies (preferably already present on the test strip) are dissolved in the remaining plasma. The antibodies are capable of binding to the peptide or polypeptide of interest, forming a three-membered sandwich complex. The antibodies (bound or unbound) flow through the strip into a detection zone. The detection zone comprises means for detecting the bound complex, e.g. it may comprise streptavidin. This immobilizes the complexes and visualizes the immobilized complex as a purple line by the gold-labeled antibody. Preferably, remaining free gold-labeled antibody may then move further down the strip where it is captured in a zone comprising a synthetic peptide or polypeptide comprising the epitope of the peptide or polypeptide of interest to be detected, visualized as a separate purple line. The presence of such second line can serve as a control because it indicates that the sample flow as worked correctly and the antibody is intact. the test strip may comprise a label indicating which peptide or polypeptide of interest can be detected with the strip. It may also comprise a barcode or other code readable by a device for optical measurement of the amount of label detectable in the detection zone. Such barcode may include information indicating which peptide or polypeptide of interest can be detected with the strip. The barcode may also include lot-specific information about the test strip.

The Cardiac Reader itself comprises a camera (e.g. a charge-coupled device camera (CCD camera)) that optically records the detection zone of the test strip. Signal and control lines may be identified by a pattern recognition algorithm. The intensity of the label in the signal line is typically proportional to the amount of peptide or polypeptide of interest. The optical signal may be converted into a concentration via a lot-specific calibration curve which may be stored in a code chip. The agreement of calibration code and test lot may be checked by a barcode on the test strip.

Furthermore, the person skilled in the art is familiar with different methods of measuring the level of a peptide or polypeptide. The term "level" relates to amount or concentration of a peptide or polypeptide in a patient or a sample taken from a patient.

The term "measuring" according to the present invention relates to determining the amount or concentration, preferably semi-quantitatively or quantitatively, of the nucleic acid, peptide, polypeptide, or other substance of interest. Measuring can be done directly or indirectly. Indirect measuring includes measuring of cellular responses, bound ligands, labels, or enzymatic reaction products. Preferably, measuring is carried out in vitro.

In the context of the present invention, amount also relates to concentration. It is evident, that from the total amount of a substance of interest in a sample of known size, the concentration of the substance can be calculated, and vice versa.

Measuring can be done according to any method known in the art. Preferred methods are described in the following.

In a preferred embodiment, the method for measuring the level of a peptide or polypeptide of interest, comprises the steps of (a) contacting a cell capable of a cellular response to the peptide or polypeptide with the peptide or polypeptide for an adequate period of time, (b) measuring the cellular response.

In another preferred embodiment, the method for measuring the level of a peptide or polypeptide of interest, particularly a BNP-type peptide, comprises the steps of (a) contacting a peptide or polypeptide with a suitable substrate for an adequate period of time, (b) measuring the amount of product.

In another preferred embodiment, the method for measuring the level of a peptide or polypeptide of interest, comprises the steps of (a) contacting a peptide or polypeptide with a specifically binding ligand, (b) (optionally) removing non-bound ligand, (c) measuring the amount of bound ligand.

Preferably, the peptide or polypeptide is contained in a sample, particularly a body fluid or tissue sample, and the amount of the peptide or polypeptide in the sample is measured.

Peptides and polypeptides (proteins) can be measured in tissue, cell, and body fluid samples, i.e. preferably in vitro. Preferably, the peptide or polypeptide of interest is measured in a body fluid sample.

A tissue sample according to the present invention refers to any kind of tissue obtained from the dead or living human or animal body. Tissue samples can be obtained by any method known to the person skilled in the art, for example by biopsy or curettage.

The term "body fluid sample" according to the invention preferably relates to a sample of blood (including derivatives thereof, e.g. blood serum or blood plasma), lymphe, cerebral liquor, saliva, or urine. More particularly, the term "body fluid sample" relates to blood (including derivatives thereof, e.g. blood serum or blood plasma) and urine. Most particularly, the term "body fluid sample" relates to blood (including derivatives thereof, e.g. blood serum or blood plasma). Samples of body fluids can be obtained by any method known and deemed appropriate.

Methods to obtain cell samples include directly preparing single cells or small cell groups, dissociating tissue (e.g. using trypsin), and separating cells from body fluids, e.g. by filtration or centrifugation. Cells according to the present invention comprise also platelets and other non-nuclear cells, e.g. erythrocytes.

If necessary, the samples may be further processed. Particularly, nucleic acids, peptides or polypeptides may be purified from the sample according to methods known in the art, including filtration, centrifugation, or extraction methods, such as chloroform/phenol extraction.

For measuring cellular responses, the sample or processed sample is added to a cell culture and an internal or external cellular response is measured. The cellular response may include the expression of a reporter gene or the secretion of a substance, e.g. a peptide, polypeptide, or a small molecule.

Other preferred methods for measurement may include measuring the amount of a ligand binding specifically to the peptide or polypeptide of interest. Binding according to the present invention includes both covalent and non-covalent binding.

A ligand according to the present invention can be any peptide, polypeptide, nucleic acid, or other substance binding to the peptide or polypeptide of interest. It is well known that peptides or polypeptides, if obtained or purified from human or animal cells, can be modified, e.g. by glycosylation. A suitable ligand according to the present invention may bind the peptide or polypeptide also via such sites.

Preferably, the ligand should bind specifically to the peptide or polypeptide to be measured. "Specific binding" according to the present invention means that the ligand should not bind substantially to ("cross-react" with) another peptide, polypeptide or substance present in the sample investigated. Preferably, the specifically bound protein or isoform should be bound with at least 3 times higher, more preferably at least 10 times higher and even more preferably at least 50 times higher affinity than any other relevant peptide or polypeptide. In the present context, such other relevant peptides or polypeptides may be other structurally related or homologous peptides or polypeptides.

Non-specific binding may be tolerable, particularly if the investigated peptide or polypeptide can still be distinguished and measured unequivocally, e.g. according to its size on a Western Blot, or by its relatively higher abundance in the sample.

Binding of the ligand can be measured by any method known in the art. Preferably, the method is semi-quantitative or quantitative. Suitable methods are described in the following.

First, binding of a ligand may be measured directly, e.g. by NMR or surface plasmon resonance.

Second, if the ligand also serves as a substrate of an enzymatic activity of the peptide or polypeptide of interest, an enzymatic reaction product may be measured (e.g. the amount of a protease can be measured by measuring the amount of cleaved substrate, e.g. on a Western Blot).

For measurement of enzymatic reaction products, preferably the amount of substrate is saturating. The substrate may also be labeled with an detectable label prior to the reaction. Preferably, the sample is contacted with the substrate for an adequate period of time. An adequate period of time refers to the time necessary for an detectable, preferably measurable amount of product to be produced. Instead of measuring the amount of product, the time necessary for appearance of a given (e.g. detectable) amount of product can be measured.

Third, the ligand may be coupled covalently or non-covalently to a label allowing detection and measurement of the ligand.

Labeling may be done by direct or indirect methods. Direct labeling involves coupling of the label directly (covalently or non-covalently) to the ligand. Indirect labeling involves binding (covalently or non-covalently) of a secondary ligand to the first ligand. The secondary ligand should specifically bind to the first ligand. Said secondary ligand may be coupled with a suitable label and/or be the target (receptor) of tertiary ligand binding to the secondary ligand. The use of secondary, tertiary or even higher order ligands is often used to increase the signal. Suitable secondary and higher order ligands may include antibodies, secondary antibodies, and the well-known streptavidin-biotin system (Vector Laboratories, Inc.)

The ligand or substrate may also be "tagged" with one or more tags as known in the art. Such tags may then be targets for higher order ligands. Suitable tags include biotin, digoxygenin, His-Tag, Glutathion-S-Transferase, FLAG, GFP, myc-tag, influenza A virus haemagglutinin (HA), maltose binding protein, and the like. In the case of a peptide or polypeptide, the tag is preferably at the N-terminus and/or C-terminus.

Suitable labels are any labels detectable by an appropriate detection method. Typical labels include gold particles, latex beads, acridan ester, luminol, ruthenium, enzymatically active labels, radioactive labels, magnetic labels ("e.g. magnetic beads", including paramagnetic and superparamagnetic labels), and fluorescent labels.

Enzymatically active labels include e.g. horseradish peroxidase, alkaline phosphatase, beta-Galactosidase, Luciferase, and derivatives thereof. Suitable substrates for detection include di-amino-benzidine (DAB), 3,3'-5,5'-tetramethylbenzidine, NBT-BLIP (4-nitro blue tetrazolium chloride and 5-bromo-4-chloro-3-indolyl-phosphate, available as ready-made stock solution from Roche Diagnostics), CDP-Star™ (Amersham Biosciences), ECF™ (Amersham Biosciences). A suitable enzyme-substrate combination may result in a colored reaction product, fluorescence or chemoluminescence, which can be measured according to methods known in the art (e.g. using a light-sensitive film or a suitable camera system). As for measuring the enzymatic reaction, the criteria given above apply analogously.

Typical fluorescent labels include fluorescent proteins (such as the fluorescent proteins derived from the jelly fish *Aequorea victoria* (e.g. GFP, YFP, RFP and derivatives thereof) or the sea pansy *Renilla reniformis*), Cy3, Cy5, Texas Red, Fluorescein, the Alexa dyes (e.g. Alexa 568), and quantum dots. Further fluorescent labels are available e.g. from Molecular Probes (Oregon).

Typical radioactive labels include 35S, 125I, 32P, 33P, 3H and the like. A radioactive label can be detected by any method known and appropriate, e.g. a light-sensitive film or a phosphor imager.

Suitable measurement methods according the present invention also include precipitation (particularly immunoprecipitation), electrochemiluminescence (electro-generated chemiluminescence), RIA (radioimmunoassay), ELISA (enzyme-linked immunosorbent assay), sandwich enzyme immune tests, electrochemiluminescence sandwich immunoassays (ECLIA), dissociation-enhanced lanthanide fluoro immuno assay (DELFIA), scintillation proximity assay (SPA), turbidimetry, nephelometry, latex-enhanced turbidimetry or nephelometry, solid phase immune tests, and mass spectrometry such as SELDI-TOF, MALDI-TOF, or capillary electrophoresis-mass spectrometry (CE-MS). Further methods known in the art (such as gel electrophoresis, 2D gel electrophoresis, SDS polyacrylamid gel electrophoresis (SDS-PAGE), Western Blotting), Can be used alone or in combination with labeling or other dectection methods as described above.

Preferred ligands include antibodies, nucleic acids, peptides or polypeptides, and aptamers, e.g. nucleic acid or peptide aptamers (e.g. spiegelmers or anticalins). Methods to obtain such ligands are well-known in the art. For example, identification and production of suitable antibodies or aptamers is also offered by commercial suppliers. The person skilled in the art is familiar with methods to develop derivatives of such ligands with higher affinity or specificity. For example, random mutations can be introduced into the nucleic acids, peptides or polypeptides. These derivatives can then be tested for binding according to screening procedures known in the art, e.g. phage display.

The term "antibody" as used herein includes both polyclonal and monoclonal antibodies, as well as variants or fragments thereof, such as Fv, Fab and F(ab)$_2$ fragments that are capable of binding antigen or hapten. The term "antibody" also includes single-chain antibodies. Antibodies capable of binding to ANP-type peptides or BNP-type peptides, particularly ANP, BNP, NT-proANP, or NT-proBNP are commercially available. Methods for generating antibodies are well-known in the are and may include immunization of suitable animals (e.g. rabbit, mouse, sheep or goat) with the peptide or polypeptide of interest (or with an immunogenic fragment thereof) or recombinant techniques.

In another preferred embodiment, the ligand, preferably chosen from the group consisting of nucleic acids, peptides, polypeptides, or aptamers, is present on an array.

Said array contains at least one additional ligand, which may be directed against a peptide, polypeptide or a nucleic acid of interest. Said additional ligand may also be directed against a peptide, polypeptide or a nucleic acid of no particular interest in the context of the present invention. Preferably, ligands for at least three, preferably at least five, more preferably at least eight peptides or polypeptides of interest in the context of the present invention are contained on the array.

According to the present invention, the term "array" refers to a solid-phase or gel-like carrier upon which at least two compounds are attached or bound in one-, two- or three-dimensional arrangement. Such arrays (including "gene chips", "protein chips", antibody arrays and the like) are generally known to the person skilled in the art and typically generated on glass microscope slides, specially coated glass slides such as polycation-, nitrocellulose- or biotin-coated slides, cover slips, and membranes such as, for example, membranes based on nitrocellulose or nylon.

The array may include a bound ligand or at least two cells expressing each at least one ligand.

In another preferred embodiment, the ligand, preferably chosen from the group consisting of nucleic acids, peptides, polypeptides, antibodies and aptamers, is present on a solid support, preferably an array. According to the present invention, the term "array" (including "gene chips", "protein chips", antibody arrays and the like) refers to a solid-phase or gel-like carrier upon which at least two compounds are attached or bound in one-, two- or three-dimensional arrangement. Solid supports or arrays comprising a ligand or binding agent for a peptide of interest are well-known in the art and include, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc. The ligand or agent may be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. Suitable methods for fixing/immobilizing said ligand or agent are well known and include, but are not limited to ionic, hydrophobic, covalent interactions and the like.

It is also contemplated to use "suspension arrays" as arrays according to the present invention (Nolan J P, Sklar L. A. (2002). Suspension array technology: evolution of the flat-array paradigm. Trends Biotechnol. 20(1):9-12). In such suspension arrays, the carrier, e.g. a microbead or microsphere, is present in suspension. The array consists of different microbeads or microspheres, possibly labeled, carrying different ligands.

The invention further relates to a method of producing arrays as defined above, wherein at least one ligand is bound to the carrier material in addition to other ligands.

Methods of producing such arrays, for example based on solid-phase chemistry and photo-labile protective groups, are generally known (U.S. Pat. No. 5,744,305). Such arrays can also be brought into contact with substances or substance libraries and tested for interaction, for example for binding or change of confirmation. Therefore, arrays comprising a peptide or polypeptide as defined above may be used for identifying ligands binding specifically to said peptides or polypeptides.

Thus, the invention also relates to the use of a diagnostic means capable of measuring, preferably in vitro, a patient's level of an ANP-type peptide (particularly NT-proANP) and/or a BNP-type peptide (particularly NT-proBNP) for diagnosing a cardiac complication due to coronary catheterization.

The invention also relates to a kit comprising a means or an agent capable of measuring an ANP-type peptide and/or a BNP-type peptide, and optionally comprising a means or agent for measuring a marker of necrosis. Such means or agent may be any suitable means or agent known to the person skilled in the art. Examples for such means or agents as well as methods for their use have been given in this specification. For example, a suitable agent may be any kind of ligand or antibody capable of specifically binding to an ANP-type peptide and/or a BNP-type peptide. The kit may also comprise any other components deemed appropriate in the context of measuring the level(s) of the respective biomarkers, such as suitable buffers, filters, etc.

Optionally, the kit may additionally comprise a user's manual for interpreting the results of any measurement(s) with respect to diagnosing a cardiac complication due to coronary catheterization. Particularly, such manual may include information about which measured level corresponds to which kind of diagnosis or which grade of risk. This is outlined in detail elsewhere in this specification. Additionally, such user's manual may provide instructions about correctly using the components of the kit for measuring the level(s) of the respective biomarker.

The invention also relates to the use of said kit for diagnosing a cardiac complication due to coronary catheterization.

The present invention also relates to the use of said kit in any of the methods according to the present invention for diagnosing a cardiac complication due to coronary catheterization.

Moreover, the invention encompasses a device for diagnosing a cardiac complication due to coronary catheterization, comprising means for measuring or capable of measuring the amount of a ANP-type peptide in a sample from the patient; and preferably, means for measuring or capable of measuring the amount of a BNP-type peptide in a sample from the patient;

preferably, means capable for determining or capable of determining a change between the measured level(s) according to a) and/or b) and measured level(s) in a different sample; and means for diagnosing or capable of diagnosing said cardiac complication by comparing the measured level to at least one reference level.

The present invention also relates to the use of such device for diagnosing a cardiac complication due to coronary catheterization.

The term "device" as used herein relates to a system of means comprising at least the aforementioned means operatively linked to each other as to allow diagnosing a cardiac complication due to corollary catheterization. Preferred means for measuring the level of a ANP-type peptide (and optionally a BNP-type peptide) and for diagnosing the risk are disclosed elsewhere in this specification in connection with the method of the invention. How to link the means in an operating manner will depend on the type of means included into the device. For example, where means for automatically measuring the level of the peptide or polypeptide of interest are applied, the data obtained by said automatically operating means can be processed by, e.g., a computer program in order to diagnose the risk. Preferably, the means are comprised by a single device in such a case. Said device may accordingly include an analyzing unit for measuring the level of the peptide or polypeptide of interest in an applied sample and a computer unit for processing the resulting data for the diagnosis. Alternatively, where means such as test stripes are used for measuring the level of the peptide or polypeptide of interest, the means for diagnosing may comprise control stripes or tables allocating the measured level to a reference level as defined elsewhere in this specification. Alternatively or additionally, the means for diagnosing may compare the measured level in a test sample to the measured level in a baseline sample and thus determine a change between said levels and compare said change to a reference change. In summary, the means for diagnosing may be adapted to carry out any step of diagnosing as laid out in this specification. The test stripes are, preferably, coupled to a ligand or agent which specifically binds to the peptide or polypeptide of interest. The strip or device, preferably, comprises means for detection of the peptide or polypeptide of interest binding to the said ligand or agent. Preferred means for detection are disclosed in connection with embodiments relating to the method of the invention above. In such a case, the means are operatively linked in that the user of the system brings together the result of the determination of the amount and the diagnostic value thereof due to the instructions and interpretations given in a manual. The means may appear as separate devices in such an embodiment and are, preferably, packaged together as a kit. The person skilled in the art will realize how to link the means without further ado. Preferred devices are those which can be applied without the particular knowledge of a specialized clinician, e.g., test stripes or electronic devices which merely require loading with a sample. The results may be given as output of a diagnostic parameter or raw data which need interpretation by the clinician. Further preferred devices comprise the analyzing units/devices (e.g., biosensors, arrays, solid supports coupled to ligands or agents capable of specifically binding to the peptide or polypeptide of interest, Plasmon surface resonance devices, NMR spectrometers, mass-spectrometers etc.) or evaluation units/devices referred to above in accordance with the method of the invention.

According to the invention the cardiac complication and/or risk may be diagnosed by comparing the measured level of the ANP-type and/or BNP-type peptide to the level measured in the baseline sample. Thus, a change of the level(s) of the ANP-type and/or BNP-type peptide may be determined. A change (increase or decrease, respectively, as compared to the baseline sample) will indicate the presence of a cardiac complication.

According to the invention, the term "concomitant" in the context of concomitant decrease or increase of an ANP-type peptide and a BNP-type peptide, respectively, is to be understood in its broadest sense. Preferably, the term is to be understood to relate to increases or decreases which refer to measurements in similar samples or the same samples. For example, a concomitant increase is also considered to have taken place if the baseline samples and/or the test samples are not the same or not taken at the same time for both markers. It will be evident to the person skilled in the art that minor differences between the times of sampling are of little importance regarding the diagnostic value of the respective increase or decrease. However, preferably the levels of the ANP-type peptide and the BNP-type peptide are determined from samples taken at the same time for each marker, or, even more preferably, from the same samples.

According to the present invention, the term "risk" relates to the probability of a particular incident, more particularly a cardiac complication, more particularly myocardial necrosis to take place. For example, a risk can be that the given incident (e.g. necrosis and/or TnT elevation) is going to take place with a probability of at least 10%, 15%, 20%, 25%, 30%, 35%, or 40% in a given patient within a particular time, e.g. the next 1 or 2 days. However, regarding symptomatic or clinically apparent cardiac complications, the respective probabilities may be lower, e.g. 1%, 2%, 3% or 5%. E.g. clinical studies can provide data further defining such risks.

The given risk can be derived e.g. from a suitable Kaplan-Meier plot for time to a given incident.

Although the risk can be expressed in absolute values, it may frequently be more useful to express the risk in relative terms, e.g. in terms of an increased risk relative to a particular given risk. The person skilled in the art is very familiar with such relative terms. For example, there is an average given risk of developing cardiac complication (particularly myocardial necrosis) in patients undergoing coronary catheterization or PCI. However, it may be more relevant to know, whether a particular patient has an additional risk of developing such cardiac complication compared to a respective comparative group (e.g. the mentioned patients undergoing coronary catheterization or PCI or a particular type of PCI), so that the total risk of this patient is "increased". Advantageously, the present invention also allows to diagnose such a relative risk.

A relative risk can be expressed in terms of hazard ratios. The term "hazard ratio" is known to the person skilled in the art. It can express the relation of the risk between two subgroups e.g. the hazard ratio between a group showing decrease of the level of an ANP-type peptide versus a group in which the level of ANP-type peptide remains stable. A difference in the hazard ratios is known as interaction to be extracted from interaction models, e.g. of risk groups with certain levels of an ANP-type peptide. The terms interaction and interaction model are known to the person skilled in the art.

Particularly, the present invention allows to identify patients at a certain risk of developing a cardiac complication, particularly myocardial necrosis. For example, the risk can be increased or not increased. The person skilled in the art is familiar with the meaning of these terms. For example, if a particular patient has a higher risk than an average patient, then the person skilled in the art will usually designate such risk as "increased".

In the context of the invention, an increased risk of developing a cardiac complication particularly myocardial necrosis, particularly relates to an increase of the risk of at least by 1.5 times, 2 times, 2.5 times or 3 times as compared to the risk of an average patient, preferably of an average patient of the same age and gender, more preferably to a patient of same age, gender, nature or etiology of cardiac disorder already present in the patient, and/or kind of coronary catheterization.

The person skilled in the art is able to determine reference changes of the levels of ANP-type peptides and/or BNP-type peptides which are associated with different kinds of diagnosis or different grades of risk.

According to the invention, the stronger the decrease of the level of the ANP-type peptide, the stronger is the likelihood that a cardiac complication is present or the higher is the risk that a cardiac complication will develop.

Preferably, the diagnosis is determined by comparing the measured change of the ANP-type or BNP-type peptide to a reference change. The term "reference" in this context is known to the person skilled in the art. Particularly, a reference change may be associated with a particular diagnosis or risk, or it may distinguish between different diagnoses or grades of risk. It will be appreciated that the reference change may also be chosen according to the desired sensitivity or specificity of diagnosis. A higher sensitivity means that a higher fraction of all patients having a particular diagnosis are identified and/or that less patients having a particular diagnosis are misdiagnosed as not having the diagnosed disorder, complication, or risk. A higher specificity means that a higher fraction of the patients identified as having a particular diagnosis do indeed have the diagnosed disease, complication, or risk. The higher the desired sensitivity for a particular diagnosis, the lower is the specificity of this diagnosis and vice versa. Therefore, the reference change may be chosen by the person skilled in the art according to the desired sensitivity and specificity. Suitable tools for choosing a reasonable reference change associated with a desired sensitivity and specificity are known in the art and include e.g. determining such change from a receiver-operator-curve (ROC).

In the context of this discussion, it is evident that a reference change may not only be a single value, but it may also include a range of values.

Particularly, the change (increase or decrease) is of a size which is considered to be significant for diagnosis, particularly statistically significant. The terms "significant" and "statistically significant" are known to the person skilled in the art. For example, to determine whether a change or level is statistically significant, a portion of patients is first identified as suffering from the disorder, complication, or risk, and the changes or levels are determined. Whether a change is statistically significant can be determined without further ado by the person skilled in the art using various well known statistic evaluation tools, e.g., determination of confidence intervals, p-value determination, Student's t-test, Mann-Whitney test, etc. Details are found in Dowdy and Wearden Statistics for Research, John Wiley & Sons, New York 1983. Preferred confidence intervals are at least 50%, at least 60%, at least 70%, at least 80%, at least 90%, at least 95%. The p-values are, preferably, 0.2, 0.1, 0.05.

More particularly, reference changes can also be derived from the changes of ANP-type or BNP-type peptides determined e.g. in studies such as presented in the examples.

Examples for reference changes of the levels are given below and in the examples. Particularly, changes of the plasma levels of NT-proANP and NT-proBNP are given which have been found in the course of the invention to be associated with or distinguishing between the indicated kinds of diagnosis or grades of risk.

It is evident, that the changes given below can serve only as a first classification of the diagnosis of a patient. For example, the final diagnosis may also be determined based on the general physical status of the patient other diagnostic parameters and the nature of the cardiac catheterization.

According to the invention, e.g. a decrease or change corresponding to a decrease of the plasma level of less than 10%, more particularly of less than 5%, most particularly of less than 2% of NT-proANP is considered to be associated with the absence of a cardiac complication or with no increased risk of developing a cardiac complication, particularly myocardial necrosis.

According to the invention, e.g. a decrease corresponding to a decrease of the plasma level of at least 5%, more particularly of at least 10% or 15%, most particularly of at least 20% of NT-proANP is associated with the presence of a cardiac complication or an increased risk of developing a cardiac complication, particularly myocardial necrosis.

It is evident that the given levels may overlap, depending on the chosen sensitivity and specificity. Therefore, according to the invention, e.g. a decrease corresponding to a decrease of the plasma level of 2% to 10%, particularly 5% to 10% of NT-proANP is able to distinguish between absence of a cardiac complication or no increased risk of developing as compared to presence of a cardiac complication or an increased risk of developing a cardiac complication. If the measured level is higher than this distinguishing level, then the measured level indicates presence of a cardiac complication or an increased risk of developing a cardiac complication. Such distinguishing level may also be called "cut-off" or "decision threshold". Such "cut-off" or "decision threshold" may tell the responsible physician whether to pursue regular treatment as planned or rather to initiate treatment or monitoring taking into account an the presence of cardiac complication or an increased risk of developing a cardiac complication, particularly myocardial necrosis.

Once the a cardiac complication or risk has been diagnosed, it may have consequences for the subsequent treatment as described below.

Preferably, a patient diagnosed according to the invention as having a cardiac complication or an increased risk should be monitored with additional care concerning the development of a cardiac complication, particularly myocardial necrosis. The person skilled in the art will understand that the final decision about treatment will be with the responsible physician who will consider additional relevant factors, such as the age of the patient, family history of cardiac disorders, the nature or etiology of a cardiac disorder present in the patient, available treatment options, the availability of monitoring possibilities etc.

If a method according to the present invention indicates no cardiac complication or no increased risk, then treatment may be continued as planned.

If a method according to the present invention indicates a cardiac complication or an increased risk, then treatment may be adapted. Preferably, treatment will be accompanied by further measuring of the level(s) of the ANP-type and/or BNP-type peptides of the invention, further measuring of marker(s) of inflammation and/or necrosis, and/or by further diagnosis, such as monitoring cardiac function at short intervals, e.g. approximately every week, preferably approximately every day, or approximately every 12 hours. Such diagnosis or monitoring may also include magnetic resonance imaging in order to localize or characterize a dysfunction. Further treatment may include administering or increasing the level of any thrombocyte aggregation inhibitors, of thrombolytic drugs, further stent implantation and any other measure deemed appropriate by the person skilled in the art. Therefore, the present invention also provides a method of treating or monitoring a patient.

The term "approximately" in the context of such time-periods or intervals is understood by the person skilled in the art. Therefore, the actual interval may also deviate from an intended regular interval depending on practical circumstances such as arranging for suitable appointments etc. Particularly the interval may e.g. deviate by up to 100%, preferably up to 50%, more preferably up to 25%, more preferably up to 10%.

Finally, the present invention also encompasses the use of the devices described herein as well as the use of an ANP-type and/or BNP-type peptide or variant thereof for diagnosing a cardiac complication due to coronary catheterization.

All references cited in this description are herewith incorporated by reference with respect to their entire disclosure content and the disclosure content specifically mentioned in this description.

The following examples illustrate the invention and are not intended to limit its scope in any way.

Example 1

Measurement of NT-proANP

NT-proANP can be determined, for example, by a competitive-binding radioimmunoassay with magnetic solid phase technique in a modification of Sundsfjord, J. A., Thibault, G., et al. (1988). Identification and plasma concentrations of the N-terminal fragment of proatrial natriuretic factor in man. J Clin Endocrinol Metab 66:605-10., using the same rabbit-anti-rat proANP polyclonal serum, human proANP (1-30) from Peninsula Lab (Bachem Ltd, St. Helene, UK) as the standard, and iodined, proANP 1-30 purified by HPLC for radio labelling. In order to achieve high sensitivity and good precision, Dynabeads M280 with sheep-anti-rabbit IgG (Dynal Biotech, Oslo, Norway) as solid phase and second antibody may be used.

In the case of the study according to Example 4, NT-proANP was measured using a commercially available ELISA test, available from Biomedica, Austria ("proANP ELISA (1-98)" Cat. No. BI-20892). The test is distributed in Germany by "Immundiagnostik Dr. Franz-Paul-Armbruster".

Example 2

Measurement of NT-proBNP

NT-proBNP is determined by an electrochemoluminescence immunoassay (Elecsys proBNP sandwich immunoassay; Roche Diagnostics, Mannheim, Germany) on Elecsys 2010. The assay works according to the electrochemoluminescence sandwich immunoassay principle. In a first step, the biotin-labelled IgG (1-21) capture antibody, the ruthenium-labelled F(ab')2 (39-50) signal antibody and 20 microliters of sample are incubated at 37° C. for 9 minutes. Afterwards, streptavidin-coated magnetic microparticles are added and the mixture is incubated for additional 9 minutes. After the second incubation, the reaction mixture is transferred to the measuring cell of the system where the beads are magnetically captured onto the surface of an electrode. Unbound label is removed by washing the measuring cell with buffer.

In the last step, voltage is applied to the electrode in the presence of a tri-propylamine containing buffer and the resulting electrochemoluminescent signal is recorded by a photomultiplier. All reagents and samples are handled fully automatically by the Elecsys® instrument. Results are determined via a calibration curve which is instrument-specifically generated by 2-point calibration and a master curve provided via the reagent barcode. The test is performed according to the instructions of the manufacturer.

Example 3

Obtaining of Samples

Blood for BNP-type peptide analysis is sampled in EDTA-tubes containing 5000 U aprotinine (Trasylol, Beyer, Germany) and Lithium-Heparin-tubes (for clinical chemistry), as appropriate. Blood and urine samples are immediately spun for 10 min. at 3400 rpm at 4° C. Supernatants are stored at −80° C. until analysis.

Example 4

Angiography was performed in 22 patients with known coronary heart disease. In all patients, the angiography showed a localized stenosis which was treated by stent implantation. Angiography and stent implantation in all patients was carried out without clinical complications.

Immediately after stent implantation (within 2 hours) a blood sample was taken. Additional blood samples were obtained after 6 and 24 hours.

The levels of NT-proANP, NT-proBNP and cardiac troponin T (cTnT, in this example also referred to as "TnT") were measured. In one group of the patients not major change in the level of NT-proANP and NT-proBNP was observed. In 12 patients a decrease of NT-proANP was observed, which was associated with a (delayed) increase of NT-proBNP. In 3 patients there was an increase of NT-proANP but no increase of NT-proBNP. In none of the patients a cardiac complication became clinically apparent. However, an increase of troponin T indicated myocardial necrosis in some patients.

The results are shown in the following table:

| | Patients N = 22 | | | |
|---|---|---|---|---|
| | Δ NT-proBNP [%] Mean NT-proBNP | Δ NT-proBNP [%] Mean NT-proBNP Time Point | Δ NT-proBNP [%] Mean NT-proBNP | Developed Troponin |
| | 0 (baseline) | 6 h | 24 h | T (+) N |
| NT-proANP, Mean | 10572.9 pg/ml | 9379.2 pg/ml | 9232.7 pg/ml | |
| Increase > 10%; N = 3 (14%) | Δ 0% 1270.3 pg/ml | Δ + 2% 1294.5 pg/ml | Δ + 2% 1293.1 pg/ml | 1 |
| Δ ± 10% N = 7 (32%) | Δ 0% 144.5 pg/ml | Δ + 13% 163.6 pg/ml | Δ + 3% 148.7 pg/ml | 0 |
| Decrease > 10%; N = 12 (55%) | Δ 0% 284.5 pg/ml | Δ + 44% 410.0 pg/ml | Δ + 41% 401.1 pg/ml | 3 |

Examples for individual patients of the study are given in the following tables:

| Pat. 1 | | | |
|---|---|---|---|
| Time Point [hours] | NT-proBNP [pg/ml] | NT-proANP [pg/ml] | TnT [pg/ml] |
| 0 | 199.5 | 10066.0 | <10 |
| 6 | 750.6 | 7848.6 | 20 |
| 24 | 637.8 | 8964.9 | <10 |

Patient No. 1 showed a decrease of NT-proANP concomitant with an increase of NT-proBNP, indicating a cardiac complication. This was confirmed by an increase of troponin T (TnT), which indicates that the complication is associated with myocardial necrosis.

| Pat. 2 | | | |
|---|---|---|---|
| Time Point [hours] | NT-proBNP [pg/ml] | NT-proANP [pg/ml] | TnT [pg/ml] |
| 0 | 448.0 | 12203.4 | <10 |
| 6 | 625.9 | 9014.4 | <10 |
| 24 | 662.1 | 11788.1 | <10 |

Patient No. 2 showed relatively constant levels of NT-proANP and NT-proBNP, indicating that there was no serious cardiac complication. This is confirmed by levels of troponin T (TnT) below cut-off, which suggests that there was no major myocardial necrosis.

| Pat. 11 | | | |
|---|---|---|---|
| Time Point [hours] | NT-proBNP [pg/ml] | NT-proANP [pg/ml] | TnT [pg/ml] |
| 0 | 171.2 | 6850.3 | <10 |
| 6 | 268.8 | 7362.1 | <10 |
| 24 | 292.5 | 4923.7 | <10 |

Patient No. 11 showed a decrease of NT-proANP concomitant with a minor increase of NT-proBNP, indicating a cardiac complication. The levels of troponin T (TnT) stayed below cut-off, which suggests that the complication was not associated with major myocardial necrosis.

| | Pat. 16 | | |
|---|---|---|---|
| Time Point [hours] | NT-proBNP [pg/ml] | NT-proANP [pg/ml] | TnT [pg/ml] |
| 0 | 2747.5 | 24470.3 | <10 |
| 6 | 2760.4 | 29364.9 | <10 |
| 24 | 2627.7 | 26085.8 | <10 |

Patient No. 16 showed relatively constant levels of NT-proANP and NT-proBNP, indicating that there was no serious cardiac complication. This is confirmed by levels of troponin T (TnT) below cut-off, which suggests that there was no major myocardial necrosis. The high absolute levels of NT-proANP and NT-proBNP indicate that there was a pre-existing cardiac insufficiency. Interestingly, the change of the levels appears to have diagnostic value largely irrespective of the degree or severity of a pre-existing cardiac insufficiency.

What is claimed is:

1. A method for diagnosing in a patient a cardiac complication caused by coronary catheterization, the method comprising the steps of
   measuring a level of NT-proANP in at least one baseline sample which has been obtained from the patient during or after coronary catheterization,
   measuring a level of NT-proANP in at least one test sample which has been obtained from the patient after coronary catheterization, and
   determining an amount of change of the level of NT-proANP between the baseline sample and the test sample, wherein a decrease in the level of NT-proANP indicates a cardiac complication.

2. The method according to claim 1, further comprising the steps of:
   measuring a level of NT-proBNP in at least one baseline sample which has been obtained from the patient during or after coronary catheterization,
   measuring a level of NT-proBNP in at least one test sample which has been obtained from the patient after coronary catheterization, and
   determining an amount of change of the level of NT-proBNP between the baseline sample and the test sample, wherein a decrease in the level of NT-proANP concomitant with an increase in the level of NT-proBNP indicates a cardiac complication.

3. The method according to claim 1 wherein the cardiac complication is selected from the group consisting of myocardial ischemia and myocardial necrosis.

4. The method according to claim 1 wherein the cardiac complication is not clinically apparent.

5. The method according to claim 4 wherein the baseline sample is obtained not later than 2 hours after coronary catheterization.

6. The method according to claim 1 wherein the test sample is obtained between 4 and 48 hours after coronary catheterization.

7. The method according to claim 6 wherein the test sample is obtained between 5 and 36 hours after coronary catheterization.

8. The method according to claim 1 wherein the decrease in the level of NT-proANP is larger than 10%.

9. The method according to claim 2 wherein the increase in the level of NT-proBNP is larger than 20%.

10. The method according to claim 2 wherein the increase in the level of NT-proBNP is larger than 25%.

11. The method according to claim 1 wherein additionally the level of a marker of necrosis is measured, wherein the marker of necrosis is selected from the group consisting of cardiac troponins, creatine kinase MB (CK-MB), and ischemic modified albumin (IMA).

12. The method according to claim 2 wherein additionally the level of a marker of necrosis is measured, wherein the marker of necrosis is selected from the group consisting of cardiac troponins, creatine kinase MB (CK-MB), and ischemic modified albumin (IMA).

13. The method according to claim 1 wherein additionally the level of a marker of inflammation is measured, wherein the marker of inflammation is selected from the group consisting of interleukins, tumor necrosis factor alpha (TNF-alpha), CRP (C-reactive protein), high sensitivity CRP (hsCRP), myeloperoxidase (MPO), monocyte chemoattractant protein-1 (MCP-1), and matrix metalloproteinases (MMPs).

14. The method according to claim 2 wherein additionally the level of a marker of inflammation is measured, wherein the marker of inflammation is selected from the group consisting of interleukins, tumor necrosis factor alpha (TNF-alpha), CRP (C-reactive protein), high sensitivity CRP (hsCRP), myeloperoxidase (MPO), monocyte chemoattractant protein-1 (MCP-1), and matrix metalloproteinases (MMPs).

15. A method for diagnosing a cardiac complication in a patient due to coronary catheterization, comprising the steps of
   measuring a level of NT-proANP in at least one baseline sample obtained from the patient during or after coronary catheterization,
   measuring a level of NT-proANP in at least one test sample obtained from the patient after coronary catheterization,
   determining a change of the level of NT-proANP between the baseline sample and the test sample, and
   determining a change of a level of NT-proBNP between the baseline sample and the test sample, wherein a decrease in the level of NT-proANP according to the determination step concomitant with an increase of level of NT-proBNP indicates a cardiac complication.

* * * * *